United States Patent
Sampson et al.

(10) Patent No.: US 6,712,815 B2
(45) Date of Patent: Mar. 30, 2004

(54) APPARATUS AND METHOD FOR TREATING VENOUS REFLUX

(75) Inventors: Russell M. Sampson, Mountain View, CA (US); Eugene Skalnyi, Mountain View, CA (US); Estela Hilario, Los Altos, CA (US)

(73) Assignee: Novacept, Inc., Palo Alto, CA (US)

( * ) Notice: Subject to any disclaimer, the term of this patent is extended or adjusted under 35 U.S.C. 154(b) by 0 days.

(21) Appl. No.: 10/052,157

(22) Filed: Jan. 16, 2002

(65) Prior Publication Data

US 2002/0143325 A1 Oct. 3, 2002

Related U.S. Application Data

(60) Provisional application No. 60/261,321, filed on Jan. 16, 2001.

(51) Int. Cl.$^7$ .............................................. A61B 18/04
(52) U.S. Cl. .......................................... 606/41; 606/49
(58) Field of Search ...................... 606/41, 45, 47–50

(56) References Cited

U.S. PATENT DOCUMENTS

| | | | |
|---|---|---|---|
| 5,047,028 A | 9/1991 | Qian ........................... 606/49 |
| 5,078,717 A | 1/1992 | Parins et al. .................... 606/48 |
| 5,318,532 A * | 6/1994 | Frassica ........................ 604/96 |
| 5,405,322 A | 4/1995 | Lennox et al. ................. 604/53 |
| 5,588,961 A | 12/1996 | Leone et al. ................... 604/21 |
| 5,609,598 A | 3/1997 | Laufer et al. ................ 606/142 |
| 5,730,136 A | 3/1998 | Laufer et al. .......... 128/661.08 |
| 5,810,847 A | 9/1998 | Laufer et al. ................ 606/142 |
| 5,938,660 A * | 8/1999 | Swartz et al. ................. 606/45 |
| 6,014,589 A | 1/2000 | Farley et al. ................. 607/98 |
| 6,033,397 A | 3/2000 | Laufer et al. ................. 606/27 |
| 6,036,687 A | 3/2000 | Laufer et al. ................. 606/27 |
| 6,071,277 A | 6/2000 | Farley et al. ................. 606/27 |
| 6,077,257 A | 6/2000 | Edwards et al. ............. 604/506 |
| 6,117,101 A | 9/2000 | Diederich et al. ............. 604/22 |
| 6,135,997 A | 10/2000 | Laufer et al. ................. 606/27 |
| 6,139,527 A | 10/2000 | Laufer et al. ............... 604/114 |
| 6,152,899 A | 11/2000 | Farley et al. ............... 604/113 |
| 6,165,172 A | 12/2000 | Farley et al. ................. 606/33 |
| 6,179,832 B1 | 1/2001 | Jones et al. ................... 606/32 |
| 6,200,312 B1 | 3/2001 | Zikorus et al. ............... 606/32 |
| 6,231,507 B1 | 5/2001 | Zikorus et al. ............. 600/437 |
| 6,237,606 B1 | 5/2001 | Zikorus et al. ............. 128/898 |
| 6,238,393 B1 * | 5/2001 | Mulier et al. ................. 606/41 |
| 6,258,084 B1 | 7/2001 | Goldman et al. ............. 606/32 |
| 6,263,248 B1 | 7/2001 | Farley et al. ................. 607/98 |
| 6,322,559 B1 | 11/2001 | Daulton et al. ............... 606/41 |
| 6,398,780 B1 * | 6/2002 | Farley et al. ................. 606/41 |
| 6,485,500 B1 * | 11/2002 | Kokish et al. ............... 606/194 |

FOREIGN PATENT DOCUMENTS

| | | | |
|---|---|---|---|
| DE | 40 01 086 A1 | 1/1990 | ........... A61B/17/22 |
| WO | WO 99/58070 | 11/1999 | ........... A61B/17/39 |
| WO | WO 01/97897 A1 | 12/2001 | .......... A61M/29/00 |

\* cited by examiner

*Primary Examiner*—Roy D. Gibson
*Assistant Examiner*—Aaron Roane
(74) *Attorney, Agent, or Firm*—Stallman & Pollock LLP

(57) ABSTRACT

Disclosed is an ablation method and apparatus used to close veins for treatment of venous insufficiency disease. The apparatus includes a catheter proportioned for insertion into a vein, a pair of inflatable balloons spaced apart on the catheter body, and an ablation electrode array disposed between the balloons. According to the disclosed method, the catheter is introduced into the vein to be treated and the balloons are distended. Blood is flushed and aspirated from the site between the balloons. RF power is applied to the electrode array, causing scarring of the vessel walls and eventual sealing of the vein.

15 Claims, 2 Drawing Sheets

APPARATUS AND METHOD FOR TREATING VENOUS REFLUX

This application claims the benefit of U.S. Provisional Application No. 60/261,321, filed Jan. 16, 2001.

FIELD OF THE INVENTION

The present invention relates generally to the field of apparatuses and methods for treating body tissue, and specifically to apparatuses and methods for treating interior surfaces of blood vessels.

BACKGROUND OF THE DISCLOSURE

Veins of the lower extremities are equipped with a series of one-way bicuspid valves that pulse open and closed. These valves facilitate flow of venous blood towards the heart and prevent venous blood from flowing away from the heart. In a condition known as venous insufficiency, defective valves do not close properly, resulting in venous reflux (backward flow of blood within the veins). Venous reflux can result in pooling of blood within the veins, and can lead to pain, swelling, ulcers, and varicose veins.

Venous reflux disease (VRD) most commonly occurs in the saphenous vein. Current treatments for VRD involve re-routing of blood from the affected vein into the nearby vasculature. In one such treatment, known as venous stripping, the long and/or short saphenous vein is removed. Another treatment for VRD involves suture ligation of the long and/or short saphenous vein. More recently other methods have been developed, including the application of RF energy to the interior of the vein, but the method is slow, requiring 30 minutes to an hour to perform, and is tedious for the physician to perform since it requires a constant, slow withdrawal of the device from the vein during the application of energy. These detriments make it impractical to perform in the clinic.

SUMMARY OF THE INVENTION

The present invention is an ablation method and apparatus used to close veins. An apparatus according to the present invention includes a catheter proportioned for insertion into a vein, a pair of inflatable balloons spaced apart on the catheter body, and an ablation electrode array disposed between the balloons. According to the disclosed method, the catheter is introduced into the vein to be treated and the balloons are distended. Blood is flushed and aspirated from the site between the balloons. RF power is applied to the electrode array, causing scarring of the vessel walls and eventual sealing of the vein. A pressure bandage may be applied around the patient's leg post-operatively for a short time to facilitate scarring and sealing.

DETAILED DESCRIPTION

Figure 1:
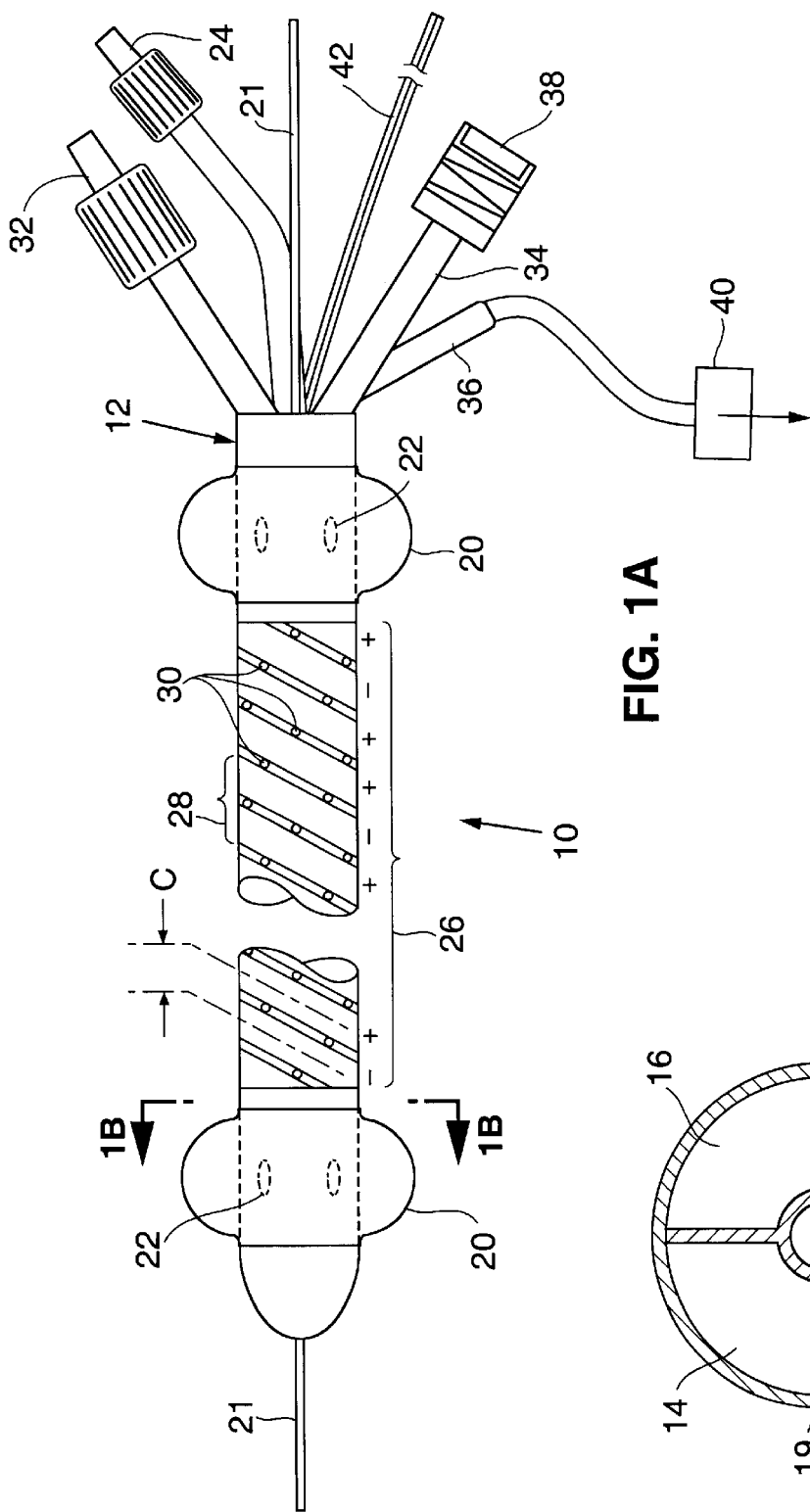
FIG. 1A is a side elevation view of an ablation catheter for treatment of venous reflux disease.
FIG. 1B is a cross-sectional side view of the catheter of FIG. 1A, taken along the plane designated 1B—1B in FIG. 1A.

Referring to FIGS. 1A and 1B, an ablation catheter 10 includes a catheter body 12, which is preferably an extrusion formed of a flexible polymeric material suitable for surgical use. Body 12 preferably includes three fluid lumens 14, 16, 18, of which lumens 16 and 18 are open to one another at the distal region of the catheter body 12. A central guidewire lumen 19 extends from the proximal end to the distal end of the catheter and receives a guidewire 21.

A pair of spaced-apart balloons 20 is disposed on the catheter body 12. The balloons are formed of an elastic or inelastic material. Each balloon is fluidly coupled to lumen 14 via small inflation openings 22 formed in the body 12. The proximal end of the lumen 14 terminates at an inflation port 24 that couples to a source of inflation medium for inflation and deflation of the balloons 20. The balloons are preferably sealed against the catheter body 12 such that when they are inflated they do not leak inflation medium directly into the vein. Lumen 14 itself is collapsible when a vacuum is applied to it.

An electrode array 26 is positioned on the catheter body 12 between the balloons 20. The array 26 includes one or more bipolar electrode pairs 28 preferably formed over the circumference of the catheter body. In a preferred configuration, the array extends along a sufficient length of catheter to permit simultaneous ablation of the full length of the targeted region of the vein. This avoids the need for repositioning the catheter within the vein, or for dragging the energized electrode through the vein to ablate the desired length of the vessel.

The electrodes preferably are constructed of a thin layer deposit using a conductive metal, for instance silver or gold. In another preferred embodiment the electrodes are constructed of a fine elastic conductive mesh with integrated insulating and conducting regions. An electrode mesh of this type is utilized on the NovaSure® Endometrial Ablation System sold by Novacept, Inc. of Palo Alto, Calif.

Figure 2:
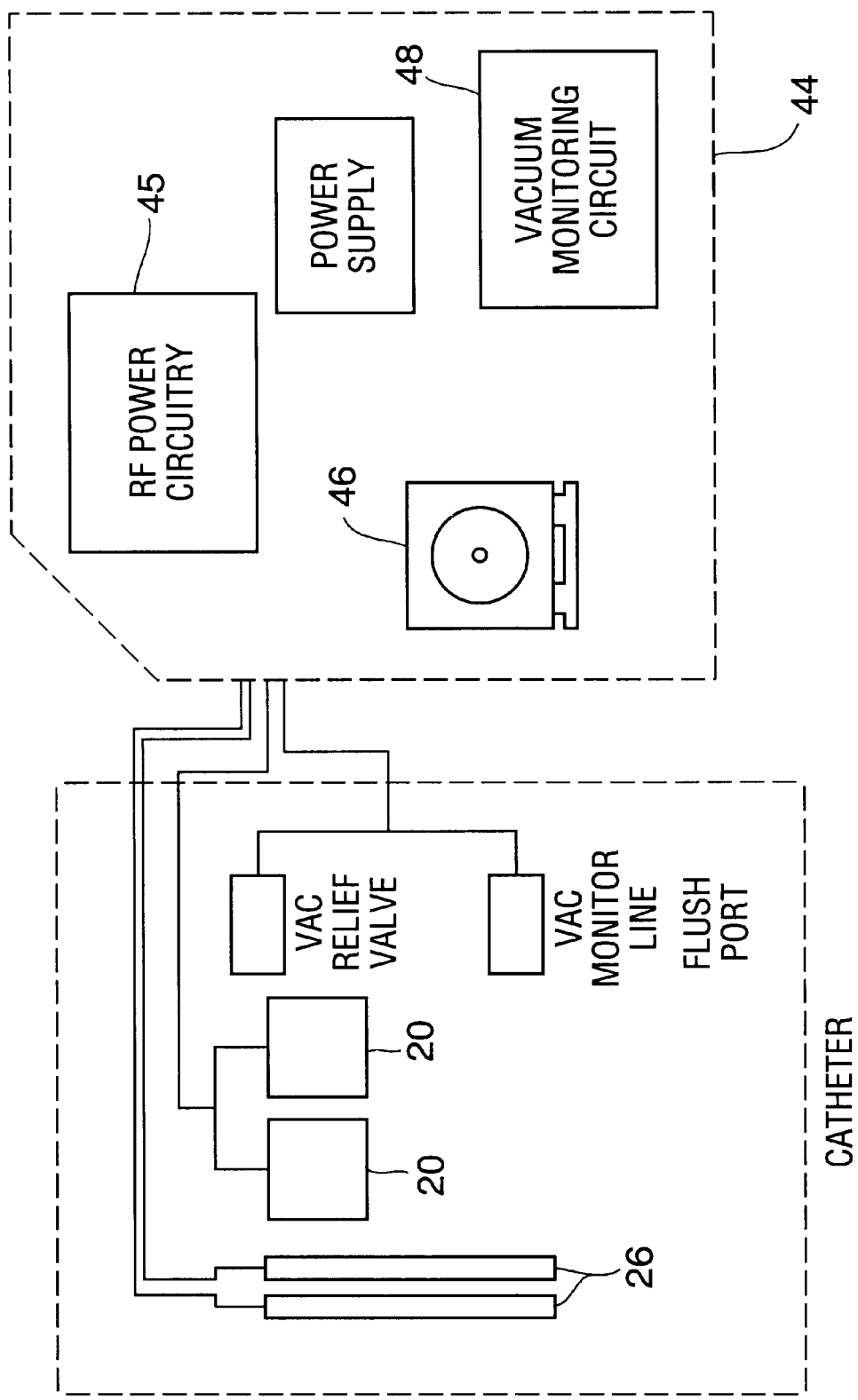
FIG. 2 is a block diagram of an ablation system utilizing the catheter of FIG. 1A.

Insulated electrode leads (not shown) extend from the electrode pairs and through the catheter body 12, and are coupled to a cable 42 that interfaces with a RF controller 44 (FIG. 2). Preferably, the RF controller 44 includes RF circuitry 45 having both low and high impedance transformation circuits, and automatically selects the impedance circuit based on real time measured impedance of the ablation electrode in contact with the vessel tissue. An impedance-matched RF generator system of this type is described in International Application No. PCT/US99/09904, Filed May 7, 1999, and entitled A RADIO-FREQUENCY GENERATOR FOR POWERING AN ABLATION DEVICE, the entirety of which is incorporated herein by reference. An RF controller employing such impedance-matching technology for ablation applications is the NovaSure® RF Controller sold by Novacept, Inc. of Palo Alto, Calif.

The center-to-center spacing C between the electrodes (i.e. the distance between the centers of adjacent electrodes), the distance between the electrodes, and the widths of the electrodes are selected so that ablation will reach predetermined depths within the tissue, particularly when controlled power is delivered through the electrodes (where power density is the power delivered per unit surface area at which low impedance, low voltage ablation can be achieved).

The depth of ablation is also affected by the electrode density (i.e., the percentage of the target tissue area which is in contact with active electrode surfaces) and may be regulated by pre-selecting the amount of this active electrode coverage. For example, the depth of ablation is much greater when the active electrode surface covers more than 10% of the target tissue than it is when the active electrode surfaces covers 1% of the target tissue.

Although the electrodes shown in the drawings are arranged in a particular pattern, it should be appreciated that the electrodes may be arranged in any pattern that will result in ablation to desired depths.

In one embodiment, the electrode spacing is approximately 0.5–1.0 mm with the active electrode surfaces covering approximately 10% of the target region. Delivery of approximately 8–10 watts of power per centimeter squared of tissue surface area using this electrode configuration will achieve ablation to a depth of approximately 0.1–2.5 mm. After reaching this ablation depth, the impedance of the tissue will become so great that ablation will self-terminate as described with respect to the operation of the system.

The proximal end of lumen 18 bifurcates into two sections of tubing 34, 36. First section 34 terminates at a vacuum relief valve 38 that regulates the vacuum level within the catheter. Second section 36 terminates at a flush port 40 that is connectable to a source of saline or other fluid that may be injected into the vein via perforations 30. Flush port 40 may also be coupled to a vacuum monitoring circuit 48, which detects the pressure within the lumen 16, 18 so as to monitor to amount of vacuum applied. In one embodiment, the vacuum pump 46 and vacuum monitoring circuit 48 may be housed within the RF controller 44, as shown in FIG. 2.

A plurality of pores/perforations 30 is formed in the catheter body 12, between balloons 20 as shown. If the array is formed of a mesh, the perforations may be the interstices of the mesh. The perforations are fluidly coupled to fluid lumens 16, 18—which may be contiguous with one other at the distal portion of the catheter body. The proximal end of lumen 16 terminates at a suction port 32 that is connectable to a vacuum pump 46. Thus, application of a vacuum to lumen 16 draws moisture and fluid through the perforations 30, through lumen 16 of the catheter body 12 and out the proximal end of the catheter body. The vacuum signal is transmitted up lumen 18, through connection 40, to the pressure transducer in the vacuum monitoring circuit 48 in the RF Controller. The vacuum monitoring circuit assures the target tissue is under the appropriate vacuum limits at appropriate times throughout the procedure. Application of a vacuum also facilitates electrode-tissue contact by drawing tissue into contact with the electrodes.

One preferred method of using the ablation catheter 10 will next be described. First, an incision is made to expose the vessel to be treated. For the saphenous vein or long saphenous vein, the incision is formed in the patient's groin. Guidewire 21 is inserted into the vein and the catheter is advanced over the guidewire 21 into the desired position within the vein. Balloons 20, 22 are inflated into contact with the interior wall of the vein, using an inflation medium introduced through port 24 and lumen 14. A flushing medium, preferably saline, is directed into flush port 40 and exits the catheter via perforations 30 where it functions to flush the region of the vessel between the balloons. It may be desirable to initiate this flow of saline prior to, or simultaneously with, insertion of the catheter to prevent blood from clogging pores/perforations 30. Suction is applied via vacuum port 32 to aspirate the mixture of saline and blood from the vein, through perforations 30 and out of the catheter. The suction in this step is preferably insufficient to collapse the vein. Flushing and aspiration are continued until much of the blood is removed from the vein, although some blood may remain in the vein without impairing operation of the catheter. A slight positive pressure, sufficient to overcome venous pressure, is maintained on the system after the flushing process is complete in order to maintain patency in perforations 30 and lumens 16 and 18.

Next, the RF controller 44 energizes the electrode array 26 to deliver ablation energy to the surrounding tissue. Suction is preferably applied to the vacuum port 32 during ablation for two reasons. First, suction collapses the vessel, thus drawing the interior wall of the vessel into contact with the electrode array. Second, suction draws moisture (gas and vapor) away from the ablation site. Moisture build-up at the ablation site may be detrimental in that it provides a conductive layer that carries current from the electrodes even when ablation has reached the desired depth. This undesirable continued current flow heats the moisture and surrounding tissue, and thus causes ablation to continue by unpredictable thermal conduction means.

Ablation causes tissue to dehydrate and thus to decrease in conductivity. By applying a vacuum or otherwise shunting moisture away from the ablation site, and thus preventing liquid build-up, there is no liquid conductor at the ablation area during use of the ablation device of the present invention. Thus, when ablation has reached the desired depth, the impedance at the tissue surface becomes sufficiently high to stop or nearly stop the flow of current into the tissue. RF ablation thereby stops and thermal ablation does not occur in significant amounts. If the RF controller is equipped with an impedance monitor, a physician utilizing the ablation device can monitor the impedance at the electrodes and will know that ablation has self-terminated once the impedance rises to a certain level. Alternatively the impedance monitor may automatically shut down power delivery after the desired impedance has been reached, and display a message or signal a type of indicator to notify the physician that the procedure is complete. By contrast, in the absence of moisture removal, the presence of liquid around the bipolar electrodes would cause the impedance monitor to give a low impedance reading regardless of the depth of ablation which had already been carried out, since current would continue to travel through the low-impedance liquid layer.

Collagen and elastin in the vessel wall may shrink during power application, collapsing the vessel down onto the catheter. Once ablation has self-terminated and/or ablation has been performed to the desired depth, delivery of RF energy to the electrodes is terminated. Relieving the pressure at connector 24 deflates balloons 20. Applying a vacuum to connector 24 then collapses lumen 14, reducing the size of the catheter to facilitate removal. The catheter is then removed from the vein. A compression bandage is applied to patient over the site of the ablation, so as to hold opposing portions of the ablated vessel in contact with one another. This causes the ablated portions of the vessel to seal against one another, thus closing the vessel and causing blood flow be diverted to surround vessels.

We claim:

1. A method of sealing a blood vessel, comprising the steps of:

providing a catheter including an elongate body, a pair of inflatable balloon members on the elongate body, and an electrode array on the elongate body between the balloons;

positioning the catheter within a blood vessel;

inflating the balloon members into contact with an interior wall of the blood vessel;

flushing blood from the portion of the blood vessel extending between the inflated balloon members;

energizing the electrode array to cause ablation of the interior wall of the blood vessel;

removing the catheter from the blood vessel; and compressing the blood vessel, causing opposed ablated regions of the interior wall to seal against one another.

2. The method of claim 1 wherein a vacuum is applied to the portion of the blood vessel extending between inflated balloon members during ablation, said vacuum collapsing the vessel, thereby drawing the interior wall into contact with the electrode array.

3. The method of claim 2 wherein the catheter elongate body includes a plurality of openings, and wherein the vacuum is applied through the openings.

4. The method of claim 1 wherein a vacuum is applied to the portion of the blood vessel extending between inflated balloon members during ablation, said vacuum drawing moisture generated during ablation away from the tissue.

5. The method of claim 4 wherein the catheter elongate body includes a plurality of openings, and wherein the vacuum is applied through the openings.

6. The method of claim 1, wherein the flushing step includes flushing the portion of the blood vessel extending between the balloon members with saline, and aspirating blood and saline from the said portion of the blood vessel.

7. The method of claim 1, wherein the catheter elongate body includes a plurality of openings, and wherein the aspirating step includes applying a vacuum to the catheter to aspirate the blood out of the vessel through the openings.

8. The method of claim 1 wherein the electrode array is a bipolar array.

9. The method of claim 1 wherein the method further includes the steps of, prior to energizing the electrode array to cause ablation:

positioning the electrode array in contact with the interior wall of the blood vessel and measuring impedance of the tissue in contact with the electrode array; and automatically selecting between a low impedance transformation circuit and a high impedance transformation circuit based on the impedance of the tissue in contact with the electrode array.

10. The method of claim 9 wherein the step of measuring the impedance of the tissue in contact with the electrode array includes providing a low-power RF signal to the electrode array.

11. The method of claim 9 wherein the step of selecting includes selecting the transformation circuit having an impedance closest to the measured impedance of the tissue in contact with the electrode array.

12. The method of claim 1 wherein the energizing step causes flow of current into the tissue, and wherein the method further includes the step of causing automatic termination of current flow into the interior wall once a selected ablation depth has been approximately reached.

13. The method of claim 12 wherein said termination occurs regardless of whether the electrode array continues to be energized.

14. The method of claim 1 wherein the removing step includes the step of collapsing the catheter into a reduced diameter step and withdrawing the collapsed catheter from the vessel.

15. The method of claim 14 wherein the collapsing step includes the step of applying a vacuum to a lumen in the catheter.

* * * * *

UNITED STATES PATENT AND TRADEMARK OFFICE
CERTIFICATE OF CORRECTION

PATENT NO. : 6,712,815 B2
DATED : March 30, 2004
INVENTOR(S) : Russell M. Sampson, Eugene Skalnyi and Estela Hilario It is certified that error appears in the above-identified patent and that said Letters Patent is hereby corrected as shown below:

Title page,
Item [75], Inventors, please correct inventor "Eugene Skalnyi's" residence as follows:
-- Eugene Skalnyi, Los Altos, CA --.

Signed and Sealed this

Twenty-seventh Day of July, 2004

JON W. DUDAS
*Acting Director of the United States Patent and Trademark Office*